United States Patent
Yamamoto

(10) Patent No.: US 8,470,729 B2
(45) Date of Patent: Jun. 25, 2013

(54) METHOD FOR STORING TITANIUM-CONTAINING SILICON OXIDE CATALYST

(75) Inventor: Jun Yamamoto, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 531 days.

(21) Appl. No.: 11/908,456

(22) PCT Filed: Mar. 13, 2006

(86) PCT No.: PCT/JP2006/305325
§ 371 (c)(1),
(2), (4) Date: Sep. 12, 2007

(87) PCT Pub. No.: WO2006/098421
PCT Pub. Date: Sep. 21, 2006

(65) Prior Publication Data
US 2009/0227807 A1    Sep. 10, 2009

(30) Foreign Application Priority Data
Mar. 17, 2005  (JP) ................................. 2005-076608
Nov. 17, 2005  (JP) ................................. 2005-332532

(51) Int. Cl.
*B01J 21/00* (2006.01)
*C07D 301/03* (2006.01)
*C07D 301/19* (2006.01)

(52) U.S. Cl.
USPC ............................ 502/242; 549/523; 549/529

(58) Field of Classification Search
USPC .................. 502/344, 64, 234, 236, 237, 239, 502/240, 242; 549/523, 529
See application file for complete search history.

(56) References Cited

U.S. PATENT DOCUMENTS

| | | | | |
|---|---|---|---|---|
| 3,923,843 | A | * 12/1975 | Wulff | 549/529 |
| 4,367,342 | A | 1/1983 | Wulff et al. | |
| 5,935,895 | A | * 8/1999 | Baiker et al. | 502/349 |
| 6,096,910 | A | * 8/2000 | Yamamoto et al. | 549/529 |
| 6,211,388 | B1 | 4/2001 | Tsuji et al. | |
| 6,252,095 | B1 | * 6/2001 | Hayashi et al. | 549/523 |
| 6,455,713 | B1 | 9/2002 | Monnier | |
| 6,753,287 | B1 | 6/2004 | Weisbeck et al. | |
| 2005/0159620 | A1 | 7/2005 | Teshigahara et al. | |
| 2006/0155137 | A1 | 7/2006 | Yamamoto | |

FOREIGN PATENT DOCUMENTS

| | | |
|---|---|---|
| JP | 2000-107604 A | 4/2000 |
| JP | 2002-524244 A | 8/2002 |
| JP | 2003-010695 | 1/2003 |
| JP | 2003-10695 A | 1/2003 |
| JP | 2003200056 * | 7/2003 |
| JP | 2004-174396 | 6/2004 |
| JP | 2004-174396 A | 6/2004 |
| JP | 2005-186065 A | 7/2005 |
| WO | WO 99/43431 A1 | 9/1999 |
| WO | 00/59849 A2 | 10/2000 |

* cited by examiner

*Primary Examiner* — Taylor Victor Oh
(74) *Attorney, Agent, or Firm* — Sughrue Mion, PLLC

(57) ABSTRACT

Provided is a method for storing a high active titanium-containing silicon oxide catalyst, characterized in that the catalyst is stored at a relative humidity of 60% or less. The method can be used for a reaction, for example, wherein an oxirane compound is prepared from hydroperoxide and olefinic compound, even after the catalyst has been stored for a long period of time. The titanium-containing silicon oxide catalyst can be suitably employed as a catalyst satisfying the following requirements: (1) an average pore diameter is 10 Å or more, (2) the pores accounting for 90% or more of the total pore volume have a pore diameter of 50 to 200 Å, and (3) a specific pore volume is 0.2 cm cm$^3$/g or more.

7 Claims, No Drawings

METHOD FOR STORING TITANIUM-CONTAINING SILICON OXIDE CATALYST

TECHNICAL FIELD

The present invention relates to a method for storing a titanium-containing silicon oxide catalyst. More particularly, the present invention relates to a method for storing a titanium-containing silicon oxide catalyst which can be used for a reaction obtaining, for example, an oxirane compound from a hydroperoxide and an olefin-type compound, and which can exhibit a high activity even after the catalyst has been stored for long period.

BACKGROUND ART

Methods of obtaining an olefin oxide compound from an olefin type compound and a hydroperoxide in the presence of a catalyst, are publicly known. As a catalyst used herein, specified titanium-containing silicon oxide catalysts are disclosed in, for example, patent literatures (e.g. U.S. Pat. Nos. 4,367,342 and 5,783,167, JP-A-7-300312, JP-A-2000-107604, JP-A-2000-107605, JP-A-2000-109469, JP-A-2000-109470, JP-A-2000-117101, JP-A-2000-119266, JP-A-2001-286768, JP-A-2002-224563, JP-A-2002-239381, JP-A-2004-195379 and JP-C-2909911). As these catalysts are used as a fixed bed catalyst, the catalysts in a large amount are filled in a reactor every several months to every several years. As the result, these catalysts are often successively produced and probably stored for long period. However, findings regarding suitable conditions under which the catalysts are stored for long time, have never been shown.

DISCLOSURE OF THE INVENTION

Under such situations, an object to be solved by the present invention is to provide a method for storing a titanium-containing silicon oxide catalyst which can be used for a reaction obtaining, for example, an oxirane compound from a hydroperoxide and an olefin-type compound, and which can exhibit a high activity even after the catalyst has been stored for a long period.

Namely, the present invention relates to a method for storing a titanium-containing silicon oxide catalyst which can be used for a reaction obtaining, for example, an oxirane compound from a hydroperoxide and an olefin-type compound and which can exhibit a high activity even after the catalyst has been stored for a long period, and is a method for storing the titanium-containing silicon oxide catalyst, which comprises storing a titanium-containing silicon oxide catalyst under a relative humidity of 60% or less.

BEST MODE FOR CARRYING OUT THE INVENTION

The titanium-containing silicon oxide catalyst to be stored for a long time, includes, for example, a one obtained by supporting a titanium source such as a titanium alkoxide, titanium halide or the like on a support such as silica gel or the like under a gas phase or liquid phase described in, for example, the above-quoted patent literatures (see U.S. Pat. No. 4,367,342 and JP-C-2909911), an aerosol type one obtained by reacting a titanium halide with a silicon halide in a flame, one obtained by a sol-gel reaction of a titanium alkoxide with a silicon alkoxide, and the like, and are not particularly limited thereto. However, it is preferable to satisfy all of the following conditions (1) to (3):

(1) an average pore diameter is 10 Å or more,
(2) pores accounting for 90% or more of the total pore volume have a pore diameter of 5 to 200 Å, and
(3) a specific pore volume is 0.2 cm$^3$/g or more.

Herein, the specific pore volume means a pore volume per 1 g of the catalyst.

Measurements of these conditions (1) to (3) can be conducted by conventional methods such as a physical adsorption method using a gas such as nitrogen, argon or the like.

The catalyst to be stored in the present invention may or may not have a peak showing an interplanar spacing (d) in an X-ray diffraction (XRD). The peak showing an interplanar spacing (d) as herein referred to, means a peak due to the crystallinity and regularity of a solid, and a broad peak due to an amorphous part may exist.

The catalyst to be stored in the present invention, preferably has an absorption peak in the region of 960±5 cm$^{-1}$ in the infrared absorption spectrum from the viewpoint of high activity. It is considered that this peak corresponds to that of titanium introduced into the silica skeleton.

The catalyst satisfying the above-described conditions (1) to (3) is preferably produced by a process comprising the following steps:

First step: a step of obtaining a solid containing a catalyst component and a template by mixing and stirring a silica source, a titanium source and the template in the liquid state;

Second step: a step of obtaining a solid containing the catalyst component by removing the template from the solid obtained in the first step; and Third step: a step of obtaining a silylated catalyst by subjecting the solid obtained in the second step to silylation.

Herein, the first step is a step of obtaining a solid containing a catalyst component and a template by mixing and stirring a silica source, a titanium source and the template in the liquid state. When the reagents used are solid, these are preferably used as a solution in which these are dissolved or dispersed in a solvent.

The silica source includes amorphous silica and alkoxysilanes, for example, tetramethylorthosilicate, tetraethylorthosilicate and tetrapropylorthosilicate. Further, silica sources having an organic group such as alkyltrialkoxysilanes, dialkyldialkoxysilanes, trialkylmonoalkoxysilanes, 1,2-bis(trialkoxysilyl)alkane and the like, can be also used. These silica sources can be used alone or may be used as a mixture of several kinds.

The titanium source includes titanium alkoxides (e.g. tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyltitanate); and titanium (IV) oxyacetylacetonate and titanium (IV) diisopropoxybisacetylacetonate; and titanium halides (e.g. titanium tetrachloride, titanium tetrabromide and titanium tetraiodide); titanyl sulfate and the like.

As the template, anyone of cationic surfactants such as alkylammoniums, dialkylammoniums, trialkylammoniums, benzylammonium and alkylpiridiniums; anionic surfactants such as alkyl sulfate ions and alkylphosphate ions, nonion surfactants such as polyalkylene oxides, block copolymer thereof and alkylamines can be applied. Among them, quaternary ammonium ions represented by the general formula (I) are preferably used.

$$[NR^1R^2R^3R^4]^+ \qquad (I)$$

(wherein, $R^1$ represents a linear or branched hydrocarbon group having 2 to 36 carbon atoms, and $R^2$ to $R^4$ represent an alkyl group having 1 to 6 carbon atoms).

$R^1$ is a linear or branched hydrocarbon group having 2 to 36 carbon atoms, preferably 10 to 18 carbon atoms.

$R^2$ to $R^4$ are respectively independently an alkyl group having 1 to 6 carbon atoms, and preferably each of $R^2$ to $R^4$ is a methyl group. Specific examples of the quaternary ammonium ion represented by the general formula (I) include cations such as hexadecyltrimethylammonium, dodecyltrimethylammonium, benzyltrimethylammonium, dimethyldidodecylammonium and hexadecylpiridinium.

In addition, the quaternary ammonium ions represented by the general formula (I) may be used alone or as a mixture of several kinds.

Examples of the solvent include water and alcohols, for example, such as methanol, ethanol, n-propanol, 2-propanol, n-butanol, sec-butanol, t-butanol, allylalcohol, cyclohexanol and benzyl alcohol, diols and mixtures thereof. The amount used of the titanium source based on the silica source is preferably from $10^{-5}$ to 1, more preferably from 0.00008 to 0.4 in terms of molar ratio. The amount used of the quaternary ammonium ion based on the total amounts of the silica source and titanium source is preferably from $10^{-2}$ to 2 in terms of molar ratio.

Further, for promoting the reaction of the silica source with the titanium source, it is preferable to impart alkalinity or acidity to the mixed solution. As the alkali source, quaternary ammonium hydroxides are preferable, and examples thereof include tetramethylammonium hydroxide, tetraethylammonium hydroxide and tetrapropylammonium hydroxide, and a hydroxide of the quaternary ammonium ion represented by the general formula (I), in which the template and the alkali source are contained in the same compound, is more preferable. Further, examples of the acid include inorganic acids such as hydrochloric acid, sulfuric acid and nitric acid, and organic acids such as formic acid, acetic acid and propionic acid.

The mixing and stirring temperature is usually from −30 to 100° C. A solid is formed by mixing and stirring, and the solid may be aged for further growth thereof. The aging time is usually 180 hours or less, and the aging temperature is usually from 0 to 200° C. When heating is required in aging, it is preferable that the mixture is transferred into a pressure vessel and heating is conducted in a closed pressure vessel for avoiding vaporization of the solvent.

Next, the second step is a step obtaining a solid containing the catalyst component by removing the template from the solid obtained in the first step.

Though the removal of the template may be carried out by any one of a high temperature calcination and solvent extraction methods, the solvent extraction method is preferable from the viewpoint of obtaining a high activity catalyst.

A technique for extracting a template with a solvent is reported by Whitehurst et al. (see U.S. Pat. No. 5,143,879)

The solvent used in extraction may include a solvent which can dissolve a compound used as the template, and oxa- and/or oxo-substituted hydrocarbons having carbon atoms of 1 to about 12 in a liquid state at room temperature can be generally used. Suitable examples of such solvents include alcohols, ketones, ethers (acyclic and cyclic) and esters. Examples thereof include alcohols such as methanol, ethanol, ethylene glycol, propylene glycol, isopropanol, n-butanol and octanol; ketones such as acetone, diethyl ketone, methyl ethyl ketone and methyl isobutyl ketone; ethers such as diisobutyl ether and tetrahydrofuran; esters such as methyl acetate, ethyl acetate, butyl acetate or butyl propionate, and the like, but, from the viewpoint of solubility to the template, alcohols are preferable, and among them, methanol is further preferable.

The weight ratio of the extracting solvent to the solid containing the catalyst component and the template is usually from 1 to 1000, preferably from 5 to 300.

Further, for improving efficiency of the extraction, an acid or a salt thereof may be added to these solvents.

Examples of acids used include inorganic acids such as hydrochloric acid, sulfuric acid, nitric acid and bromic acid, and organic acids such as formic acid, acetic acid and propionic acid. Further, examples of salts thereof include alkali metal salts, alkaline earth metal salts and ammonium salts.

The concentration in the solvent of the acid or salt thereof to be added is preferably 10 mol/l or less, further preferably 5 mol/l or less. When the concentration in the solvent of the acid or salt to be added is too high, the catalytic activity may be lowered by elution of titanium in the catalyst.

After adequately mixing the solvent with the solid containing the catalyst component and the template, a liquid phase part is separated by a method of filtration, decantation or the like. This operation is repeated required times. Further, it is also possible to extract the template by a method of filling the solid containing the catalyst component and the template in a tube or the like and passing an extraction solvent through there. Completion of the extraction can be known by, for example, analyzing the liquid phase part. The extraction temperature is preferably 0 to 200° C., further preferably 20 to 100° C. When the boiling point of the extraction solvent is low, the extraction may be carried out under pressure.

The quaternary ammonium ion represented by the general formula (I) obtained after the extraction treatment can be recycled as a template material in the first step after recovery. In addition, likewise the template, the solvent used for extraction can be purified through a usual distillation operation or the like and also recycled.

Alcohols suitably used for the template removal damages the desired reaction because those react with the silylating agent in the next silylation step, therefore, the extracting agent contained in the solid after the template removal is usually removed by a drying operation. As a drying apparatus, a conical dryer and plate dryer equipped with a hot-air device or vacuum device, are listed. However, since it require a considerable time to conduct the drying economically efficiently, it may be not sufficient from the viewpoint of productivity of the catalyst. In addition, a performance of the catalyst may deteriorate because a shrinkage of pores, a change of catalyst surface properties and the like occur depending on drying conditions.

For efficiently producing the catalyst, it is preferable to substitute the solvent contained in the solid obtained in the second step with a solvent substantially inactive to the silylating agent to be used in the successive silylating step. The substitution solvent used in the substitution step may be a solvent satisfying conditions of which it is substantially inert to the silylating agent and it can dissolve the extracting solvent used in the second step.

The solvent suitably used in the substitution operation, generally includes hydrocarbons, halogenated hydrocarbons, ketones, ethers, esters, N,N-substituted amides, nitrites and tertiary amines having 1 to about 12 carbon atoms and showing a liquid state at ordinary temperature, for example, hexane, cyclohexane, chloroform, benzene, toluene, xylene, acetone, diethylketone, methylethylketone, methylisobutylketone, diethylether, diisobutylether, tetrahydrofuran, dioxane, methylacetate, ethylacetate, dimethylformamide, acetonitrile, pyridine, triethylamine and dimethylsulfoxide. A preferable solvent for substitution is hydrocarbons in connection with the subsequent silylation step, and among them, toluene is further preferable. These solvents can be used respectively alone or as a mixture solution of several kinds.

In the substitution operation, after the substitution solvent and the solid containing the extracting solvent obtained in the second step have been thoroughly mixed, a liquid phase part formed is separated by a method of filtration, decantation or the like. This operation is repeated required number of times. Further, it is also possible to substitute with the extracting solvent by a method of filling a reaction tube or the like with the solid containing the extracting solvent and then passing the substitution solvent through the solid.

The second step and the solvent substitution step, further, additionally the successive silylating step are preferably conducted with the same reactor from the viewpoint of productivity of the catalyst. Completion of the substitution operation can be known by, for example, analysis of the liquid phase part. The substitution temperature is preferably 0 to 200° C., more preferably 20 to 100° C. When the boiling point of the solvent used in the operation is low, the operation may be conducted under pressure.

In addition, the solvent for substitution used in the substitution step can be recycled after removing the extracting agent by a conventional method such as distillation, extraction or the like.

Further, the third step is a step of obtaining a silylated catalyst by subjecting the solid obtained in the second step to silylation treatment.

The silylation may be carried out by a gas phase method in which the titanium-containing silicon oxide is reacted with a gaseous silylating agent, or a liquid phase method in which a silylating agent is reacted with the titanium-containing silicon oxide in a solvent, but, the liquid phase method is more preferable. Usually, when the silylation is carried out by the liquid phase method, hydrocarbons are preferably used.

Examples of the silylation agent include organic silanes, organic silylamines, organic silylamides and derivatives thereof, organic silazanes and other silylation agents.

Examples of the organic silane include chlorotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane and 3-cyanopropyldimethylchlorosilane.

Examples of the organic silylamine include N-trimethylsilyldimethylamine, N-trimethylsilyldiethylamine, N-triethylsilylamine, N-triethylsilyldimethylamine, N-triethylsilyldiethylamine, N-tri-n-propylsilylamine, N-tri-t-butylsilylamine, N-trimethylsilylimidazole, N-triethylsilylimidazole, N-tri-n-propylsilylimidazole, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane and pentafluorophenyldimethylsilylamine.

Examples of the organic silylamide and derivatives thereof include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutylamide, N-(t-butyldimethylsilyl)-N-trifluoroacetamide and N,O-bis(diethylhydrosilyl)trifluoroacetamide.

Examples of the organic silazane include hexamethyldisilazane, hexaethyldisilazane, heptamethyldisilazane, 1,1,3,3-tetramethyldisilazane, 1,3-bis(chloromethyl)tetramethyldisilazane, 1,3-divinyl-1,1,3,3-teteramethyldisilazane, 1,3-diphenyltetramethyldisilazane and hexamethylcyclotrisilazane.

Examples of the other silylation agent include N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate, triethylsilyltrifluoromethane sulfonate and N,N'-bistrimethylsilylurea. The silylating agents may be used alone, two or more kinds thereof may be used at the same time or separately. The most preferable silylation agent is hexamethyldisilazane. Further, the above-described silylation may be conducted by any method of a batch form or flowing form.

It is preferable to dry the catalyst after the silylation by a common method of which the catalyst is contacted with an inert dried gas such as nitrogen dried under reduced pressure or heated, or the like.

The catalyst to be suitably stored in the present invention is usually processed into a molded catalyst via a step for molding a solid containing the catalyst component. Though the molding step may be conducted in any stage, namely, before or after the above-mentioned template-removing step, after the solvent substitution step, and after the silylation step, it is preferable to conduct before the template-removing step from the viewpoint of suppression of degradation of catalyst properties such as specific surface area and pore volume. As the molding method, any method such as compression molding or extrusion molding may be used. An organic or inorganic binder usually used can be used in the extrusion molding, but lowering of catalyst activity may be caused by addition of the binder. In the production of the molded catalyst, the compression molding is the most preferable from the viewpoint of strength and physical properties of the catalyst.

As the compression molding, a roll press molding (briquetting, compacting), oil hydraulic press molding, tabletting and the like can be listed. The pressure in compression is usually 0.1 to 10 ton/cm$^2$, preferably 0.2 to 5 ton/cm$^2$, and further preferably 0.5 to 2 ton/cm$^2$. When the pressure is too low, the strength of a molded body is sometimes inadequate. On the other hand, when the pressure is too high, the physical properties of the catalyst sometimes become inadequate because pores are broken. In carrying out the compression molding, it is preferable that a solid containing a catalyst component contains water in a proper amount, and this can produce a molded body having a sufficient strength under a lower compressing pressure. The water content of the material to be subjected to the compression molding is preferably 1 to 70% by weight, further preferably 5 to 40% by weight. The water amount may be adjusted by a dryness degree during drying of a wet solid, and may be adjusted by adding water to an adequately dried solid.

In addition, a binder usually used or the like may be added within a range of no obstacle to a desired performance.

The shape of the molded body may be any shape such as tablet, sphere or ring. Further, the molded body may be used as it is or after pulverizing to a proper size.

The catalyst can be used for selective oxidation, for example, in addition to epoxidation of an olefin, various oxidation reactions of organic compounds because the catalyst has a high specific surface area and highly dispersed titanium active sites. Further, if desired, it is also possible to intensify acid sites of the catalyst with addition of a third component such as alumina, etc., and the catalyst can be used for alkylation, catalytic reforming, etc.

The method for storing the catalyst of the present invention is characterized by storing the catalyst under a relative humidity of 60% or less, and it is preferable to store the catalyst under a relative humidity of 30% or less, and more preferably 15% or less. When the relative humidity during store is too high, remarkable deterioration of a catalytic activity is caused.

A method of adjusting the relative humidity to a desired value includes a method of continuously flowing a drying gas in a container in which the catalyst is charged, a method of storing a catalyst in a container in which the catalyst is sealed together with a drying agent such as a silica gel, zeolite or the like, a method of storing a catalyst in a container and/or storage equipped with a moisture controller, a method of hermetically storing a catalyst after adjusting the humidity in a container having a gas barrier property to a desired value, and the like. Herein, the storage period of the catalyst means a period from completion of the catalyst production to use of the catalyst for a reaction, generally, a period between the time the catalyst is charged in a storage container after it has been produced and the time the container is opened for introducing the catalyst into a reactor.

As a material of the container, any material which can maintain the dried state is used, for example, glass, metals such as iron and aluminum, resins such as acrylate resin, polyethylene terephthalate, polybutylene terephthalate, polyesters and other resins having a gas barrier property such as engineering plastics, and resins in which a resin having a gas barrier property is laminated on and resins in which a metal such as aluminum is laminated on can be listed.

Among them, a container in which a inner bag prepared from a resin laminated with aluminum is worn is suitably used. A gas of storing atmosphere is not particularly restricted if it does not contain a substance having harmful effects, and if the conditions mentioned in the description are satisfied, there is no problem. In general, air, nitrogen, oxygen, argon, carbon dioxide or the like is preferably used, among them, to use air or nitrogen from the viewpoint of safety is more preferred.

The temperature during storing is preferably −30 to 100° C., preferably 0 to 40° C., but should not be limited thereto.

The catalyst stored in the present invention can be most preferably used for a process of producing an oxirane compound through a reaction of an olefin-type compound with a hydroperoxide, in particular.

The olefin type compound may be acyclic, mono-cyclic, di-cyclic or poly-cyclic compounds, and mono-olefin type, di-olefin type or poly-olefin type compounds. When the number of olefin bonds is two or more, these may be a conjugated bond or non-conjugated bond. Olefin type compounds having 2 to 60 carbon atoms are usually preferred. Examples of such the hydrocarbon include ethylene, propylene, 1-butene, isobutylene, 1-hexene, 2-hexene, 3-hexene, 1-octene, 1-decene, styrene and cyclohexene. Appropriate examples of the diolefin-type compound include butadiene and isoprene. Further, the olefin-type compound may have a substituent, and the substituent is preferably a relatively stable group. An example thereof includes a halogen atom, further various substituents containing an oxygen, sulfur or nitrogen atom together with a hydrogen and/or carbon atom, may exist. A particularly preferable olefin type compound is an olefin type unsaturated alcohol and an olefin type unsaturated hydrocarbon substituted with a halogen, and as examples thereof, allyl alcohol, crotyl alcohol, allyl chloride are listed.

As examples of a hydroperoxide, organic hydroperoxides can be listed.

The organic hydroperoxide is a compound represented by the general formula;

(wherein, R represents a monovalent hydrocarbon group), and is reacted with an olefin type compound to produce an oxirane compound and compound, R—OH. Preferably, the group R is a group having 3 to 20 carbon atoms. Further preferably, R is a hydrocarbon group having 3 to 10 carbon atoms, particularly a secondary or tertiary alkyl group or aralkyl group. Among them, tertiary alkyl groups and secondary or tertiary aralkyl groups are particularly preferable, and specific examples thereof include a tertiary butyl group, tertiary pentyl group, cyclopentyl group, and 2-phenylpropyl-2 group. Further, various tetralinyl groups formed by eliminating a hydrogen atom from an aliphatic side chain of a tetralin molecule, are also listed.

When cumene hydroperoxide as the organic hydroperoxide is used, the resulting hydroxyl compound is 2-phenyl-2-propanol. This can be converted into α-methyl styrene by dehydration reaction. α-methyl styrene obtained is converted into cumene by a reaction with hydrogen in the presence of a catalyst, further, cumene obtained can be converted into cumene hydroperoxide by a reaction with oxygen, and it can be used for a reaction with an olefin-type compound.

When ethylbenzene hydroperoxide as the organic hydroperoxide is used, the resulting hydroxyl compound is 1-phenylethanol. This can be converted into styrene by dehydration reaction.

Styrene is useful as a raw material of resins such as polystyrene and an ABS resin. Further, styrene obtained is converted into ethylbenzene through a reaction with hydrogen in the presence of a catalyst, furthermore, ethylbenzene obtained can be converted into ethylbenzene hydroperoxide by a reaction with oxygen, and it can be used for a reaction with an olefin-type compound.

Tertiary amylene formed by dehydration of tertiary pentyl alcohol obtained by using tertiary pentyl hydroperoxide as the organic hydroperoxide, is a useful substance as a precursor of isoprene. Tertiary pentyl alcohol is also useful as a precursor of methyl tertiary pentyl ether which is an octane booster.

Tertiary butyl alcohol obtained by using t-butyl hydroperoxide as an organic hydroperoxide is useful as a precursor of methyl tertiary butyl ether which is an octane booster.

Hydrogen peroxide can be listed as an example other than organic hydroperoxides.

Hydrogen peroxide is a compound represented by the chemical formula, HOOH, and can be obtained usually in the form of an aqueous solution. It reacts with an olefin type compound to form an oxirane compound and water.

The organic hydroperoxide and hydrogen peroxide, which are used as a raw material, may be a thin or dense purified or non-purified material. Between them, the organic hydroperoxide is preferably used in the present invention, The epoxidation can be carried out in a liquid phase by using a solvent and/or a diluent. The solvent and diluent are a substance which is liquid under the pressure and temperature under which the reaction is conducted, and must be substantially inert against the reactants and products. The solvent may be a substance existing in the hydroperoxide solution to be used. For example, when cumene hydroperoxide is a mixture of cumene hydroperoxide and cumene which is a raw material thereof, said cumene hydroperoxide can be used as a substitute for the solvent without especially adding a solvent.

The epoxidation temperature is usually from 0 to 200° C., preferably from 25 to 200° C. The pressure may be a pressure enough to keep the reaction mixture liquid. Usually, the pressure is advantageously from 100 to 10000 kPa.

After completion of the epoxidation, a liquid mixture containing a desired product can be easily separated from a catalyst. Next, the liquid mixture can be purified by a suitable method. Purification includes fractional distillation, selective extraction, filtration, washing and the like. The solvent, catalyst, non-reacted olefin type compound and non-reacted hydroperoxide can be used again by recycling.

The reaction, in which the catalyst of the present invention is used, can be carried out in the form of a slurry or a fixed bed, and, in the case of a large scale of industrial operation, it is preferable to use a fixed bed. The present process can be carried out by a batchwise method, semi-continuous method or continuous method. When a solution containing a reactant is introduced through a fixed bed, a liquid mixture obtained from a reaction zone does not contain catalyst at all or contains substantially no catalyst.

EXAMPLE

The present invention is illustrated by the following Examples below.

Example 1

Preparation of Catalyst Powder (First Step)

While stirring 125.1 parts by weight of an aqueous solution of 16% by weight of hexadecyltrimethyl ammonium hydroxide (containing 25% by weight of methanol), a mixed solution of 1.85 parts by weight of tetra-isopropyl orthotitanate and 10.0 parts by weight of 2-propanol was added dropwise to this at 40° C. After stirring of 30 minutes, 38.1 parts by weight of tetramethyl orthosilicate was added dropwise. Thereafter, stirring was continued at 40° C. for 1 hour. Thus obtained precipitate was filtered. The precipitate obtained was dried at 70 under vacuum.
Preparation of Molded Body A mixture obtained by sufficiently mixing 10.0 parts by weight of the white solid obtained by drying with water with a spray so that the water content became 1.5 parts by weight, was subjected to compression molding.

The obtained solid was pulverized, and then molded body containing the catalyst component and template of 1.0 to 2.0 mm was obtained using sieves. Solid smaller than 1.0 mm was recycled to conduct compression molding again.
Extractive Removal of Template (Second Step)

Next, 10.0 parts by weight of the molded body obtained as described above was packed in a glass-lining column, (1) 91.1 parts by weight of methanol at room temperature, (2) 168.1 parts by weight of 0.2 mol/l-hydrochloric acid methanol solution under heating of 45° C., and (3) 132.3 parts by weight of methanol under heating of 45° C., in this order, were respectively passed through the column at LHSV of 6 h$^{-1}$ upwardly. After completion of passing through, methanol in the column was drawn from the bottom of the column. Thereafter, the molded catalyst was dried under vacuum at 110° C.
Silylation (Third Step)

The solid obtained of 5.0 g, hexamethyldisilazane of 3.4 g and toluene of 30.0 g were charged in a flask, and then, syliation was carried out under heating of 110° C. for 1.5 hours. After separating the solvent by decantation, a titanium-containing silicon oxide catalyst was obtained by heating at 110° C. under vacuum.
Storing of Catalyst The titanium-containing silicon oxide catalyst described above was charged in a 20 ml-sample bottle made of glass and the inner atmosphere of the bottle was substituted with dried nitrogen, thereafter, the catalyst was hermetically stored for one week.
Synthesis of Propylene Oxide (PO)

The catalyst obtained as described above was evaluated with a batch reaction apparatus (autoclave) using a cumene solution containing 25% of cumene hydroperoxide (CHPO) and propylene (C3'). 1.0 g of the catalyst, 30.0 g of CHPO and 16.6 g of C3' were charged in the autoclave to react them under autogenous pressure at a reaction temperature of 85° C. for a reaction time of 1.5 hours (containing temperature raising time). The reaction result is shown in Table 1.

Example 2

The catalyst obtained by the same operation as in Example 1 except that storing was carried out in a opened system at a temperature of 20±5° C. and a relative humidity of 50±5% for 6 months, was evaluated with a batch reaction apparatus in the same manner as in Example 1.
The reaction result is shown in Table 1.

Comparative Example 1

The catalyst obtained by the same operation as in Example 1 except that storing was carried out in a opened system at a temperature of 50° C. and a relative humidity of 85% for 2 months, was evaluated with a batch reaction apparatus in the same manner as in Example 1.

TABLE 1

|  | Example 1 | Example 2 | Comparative Example 1 |
|---|---|---|---|
| Storage | hermetically stored at room temperature for one week in a sample bottle | Relative humidity: 50 ± 5% Temperature: 20 ± 5° C. Opened system for 6 months | Relative humidity: 85% Temperature: 50° C. Opened system for 2 months |
| Increase of weight % *1 | 0.0 | 0.3 | 8.4 |
| Reaction result |  |  |  |
| CHPO Conversion % | 97.0 | 96.8 | 29.2 |

TABLE 1-continued

|  | Example 1 | Example 2 | Comparative Example 1 |
|---|---|---|---|
| PO Selectivity *2 | 98.4 | 97.6 | 96.3 |
| PG's Selectivity *3 | 1.6 | 2.4 | 3.6 |

*1: (Weight after storage − Weight before storage)/Weight before storage × 100
*2: Produced PO mole/Reacted C3' mole × 100
*3: Produced (propylene glycol + 2 × di-propylene glycol + 3 × tri-propylene glycol) mole/Reacted CHPO mole × 100

INDUSTRIAL APPLICABILITY

According to the present invention, a method for storing a titanium-containing silicon oxide catalyst which can be used for a reaction obtaining, for example, an oxirane compound from a hydroperoxide and an olefin-type compound, and which can exhibit a high activity even after the catalyst has been stored for a long period, can be provided.

The invention claimed is:

1. A method for storing a titanium-containing silicon oxide silylated catalyst, which comprise storing the catalyst at a relative humidity of 15% or less,
wherein the catalyst is used for a reaction obtaining an oxirane compound from a hydroperoxide and an olefin compound, and
wherein titanium is the only transition metal contained in the catalyst.

2. The method according to claim 1, wherein the catalyst satisfies the following conditions (1) to (3):
(1) an average pore diameter is 10 Å or more,
(2) pores accounting for 90% or more of the total pore volume have a pore diameter of 5 to 200 Å, and
(3) a specific pore volume is 0.2 cm³/g or more.

3. The method according to claim 2, wherein the catalyst has been produced by the following steps:

first step: a step of obtaining a solid containing a catalyst component and a template by mixing and stirring a silica source, a titanium source and the template in a liquid state;
second step: a step of obtaining a solid containing the catalyst component by removing the template from the solid obtained in the first step; and
third step: a step of obtaining a silylated catalyst by subjecting the solid obtained in the second step to silylation.

4. The method according to claim 3, wherein the template used in the first step is a quaternary ammonium ion represented by the formula (I):

$$[NR^1R^2R^3R^4]^+ \quad (I)$$

(wherein, $R^1$ represents a linear or branched hydrocarbon group having 2 to 36 carbon atoms, and $R^2$ to $R^4$ respectively independently represent an alkyl group having 1 to 6 carbon atoms).

5. The method according to claim 3, wherein the removal of the template is carried out by solvent extraction operation.

6. The method according to claim 3, further comprising a step of molding the solid containing the catalyst component.

7. The method according to claim 1, wherein the catalyst is a catalyst obtained by supporting a titanium alkoxide or titanium halide on a silica gel support.

* * * * *